United States Patent [19]

Buchanan

[11] Patent Number: 4,618,629

[45] Date of Patent: Oct. 21, 1986

[54] FRAGRANCE-EMITTING POLYURETHANE FOAMS

[75] Inventor: Michael S. Buchanan, Baltimore, Md.

[73] Assignee: Wm. T. Burnett & Co., Inc., Baltimore, Md.

[21] Appl. No.: 739,075

[22] Filed: May 29, 1985

[51] Int. Cl.$^4$ .............................................. C08G 18/14
[52] U.S. Cl. ....................................... 521/76; 521/137
[58] Field of Search ................................... 521/76, 137

[56] References Cited

U.S. PATENT DOCUMENTS

| 4,226,944 | 10/1980 | Stone et al. | 521/122 |
| 4,309,509 | 1/1982 | Wood | 521/137 |
| 4,327,194 | 4/1982 | Chandalia et al. | 521/137 |

Primary Examiner—Maurice J. Welsh
Attorney, Agent, or Firm—A. W. Breiner

[57] ABSTRACT

Polyurethane foams having a particulate resin carrying a fragrance incorporated therein during formation of the foam are described. The physical characteristics of the foams are not detrimentally affected by the incorporation of the resin while providing a foam which will release fragrance over an extended time period.

18 Claims, No Drawings

FRAGRANCE-EMITTING POLYURETHANE FOAMS

FIELD OF INVENTION

This invention relates to polyurethane foams which will emit a fragrance and to a method of making such foams. More particularly, the present invention is directed to polyurethane foams having a particulate resin containing a fragrance incorporated therein during formation of the foam, whereby the fragrance is released at a slow rate over time.

BACKGROUND OF INVENTION

Fragrance-emitting devices or articles such as air fresheners are known. Practically, such devices or articles must emit the fragrance at a controlled rate over a prolonged period of time. Moreover, it is particularly desirable that the device or article is designed in order that the fragrance is not emitted to the atmosphere until wanted or needed. This is usually accomplished by enclosing the fragrance-emitting article in a vapor-impermeable package, with the package being opened, exposing the fragrance-emitting article or device to the atmosphere when the article or device is placed in use. This requires, therefore, that the fragrance emitted from the article or device reach an equilibrium within the enclosed package permitting prolonged storage of the device while enclosed, with activation occurring only when the package is opened.

Foams including polyurethane foams, because of their low cost and ready availability, have been suggested for use as or in fragrance-emitting articles or devices. It has been generally recognized, however, that while perfumes or fragrance bearing foams can be made by impregnating pre-made foams with a fragrance-emitting material, such foams have only short life before the fragrance is exhausted from a use standpoint. Additionally, large amounts of the fragrance material is lost in the preparation of the perfumed foam. It has also been proposed that a fragrance material be incorporated into a polyurethane foam during the foam-forming process. It has been found, however, that the fragrance material being a high volatile or relatively high volatile substance is volatilized during the formation of the foam due to the highly exothermic reaction which occurs during foaming. Therefore, not enough fragrance remains in the foam for practical application. Additionally, the evolution of the fragrance material during foaming can detrimentally affect the physical characteristics of the foam.

It has also been proposed in U.S. Pat. No. 4,226,944 that foams can be made by mixing the fragrance material with a dry particulate filler, adding this premix to a liquid polyol to form a second mixture, and then introducing the second mixture into a reaction zone together with an organic di- or polyisocyanate, a blowing agent, and a catalyst to produce a polyurethane foam-forming reaction mixture. The dry particulate material as disclosed in the patent can be clay, limestone, soap, detergent, or mixtures thereof. These particulate materials have a pre-existing structure, possibly porous, and, accordingly, the liquid fragrance material will either be adsorbed or absorbed to the surface of the particles or into the pores of the particles if porous. While foams produced according to the patent allegedly will emit the fragrance over a protracted period of time at ambient conditions and since the fragrance material is premixed with the dry particulate filler at the time of the foaming with the fragrance material being thereby adsorbed or absorbed by the filler, there still will be a substantial loss of the volatile perfume during the foaming operation. Again the evolution of the volatile substance can detrimentally affect the physical characteristics of the foam, including uniform cell size, freedom from pinholing, good structural stability, and strength.

PRIMARY OBJECTS AND GENERAL DESCRIPTION OF INVENTION

Accordingly, it is a primary object of the present invention to provide a polyurethane foam having fragrance-emitting characteristics, with the fragrance being emitted over a prolonged period of time.

It is another primary object of the present invention to provide a polyurethane foam having uniformly incorporated in the foam a fragrance-emitting substance which will release the fragrance at a controlled rate over a protracted period of time.

It is another primary object of the present invention to provide a polyurethane foam having a fragrance material uniformly incorporated therein which can be enclosed in a vapor-impermeable package, with the fragrance-emitting characteristic being activated by opening the package.

The above and other objects of the present invention are accomplished by providing a polyurethane foam formulation comprising in intimate admixture a polyether or polyester polyol, a polyisocyanate, and a resin in finely divided form having a fragrance-emitting material incorporated therein and, thereafter, foaming the formulation in the presence of water. During the foaming reaction of the foam-forming components, the finely divided resin carrying the fragrance material is uniformly incorporated in the foam. There is little or no loss of the frarance material during foaming. Although it is not known whether the resin is chemically bonded to the foam or merely absorbed in the polyurethane foam polymer, it is apparent that the resin is bonded to the foam to the extent that it is not leached out. Moreover, foams produced according to this invention have excellent foam characteristics, including uniform cell size, freedom from pinholing or other detrimental characteristics often associated with incorporation of the foreign material into the foam formulation during the in situ preparation of the foam. It has also been found that the density of the foam and other foam characteristics can be varied as in a conventional foam which does not include the resinous fragrance material. Thus, foams can be provided having a density of from as low as about 1.2 to about 6 pounds per cubic foot, with the softness or firmness of the foam also being modified. Further, the cell size of the foam can be controlled to provide either a fine cell, non-clickable foam or a coarse cell, clickable foam.

It has been found that the foams made according to the present invention, in addition to having good foam properties, will emit fragrance up to a minimum of about three months. It has also been found that the foams can be enclosed in a vapor-impermeable package and stored for an indefinite period. After storage and upon opening of the package, the foam article will emit fragrance for the same, or substantially the same prolonged period. Apparently once the vapors of the fragrance material saturates the air within the package, further emission of vapors is retarded until the package is opened and the foam exposed to the atmosphere. This is an important feature from a practical standpoint.

The resins which can be utilized to carry the fragrance according to the present invention are solid, organic, macromolecular, thermosetting, or thermoplastic resins containing up to about 70 percent by weight fragrance material. These resin compositions are easily prepared and readily stored in vapor-impermeable packages for subsequent use. The term "solid organic macromolecular, thermoplastic, and thermosetting resins" as the term is used herein means polymers of thermoplastic or thermosetting character having a molecular weight of preferably above about 1000 and which are solids at room temperature. Exemplary of such materials are the polyolefins such as polyethylene, polypropylene and copolymers thereof; acrylate ester resins such as polymethylacrylate, polyethylacrylate, polymethylmethacrylate, polyethylmethacrylate, polyhydroxyethylacrylate, and copolymers thereof; vinyl resins such as polystyrene; polyvinyl halides such as polyvinyl chloride; polyvinyl acetals such as polyvinyl butyral; polyvinylidene compounds such as polyvinylidene chloride; polyamide resins; synthetic and natural elastomers such as polyisoprene, polybutadiene; cellulose plastics such as cellulose acetate, cellulose butyrate, cellulose nitrate, and the like. Choice of the resin will depend both on the particular fragrance material which is to be formulated into the resin and the conditions under which the final formulation will be employed. The resin or class of resins preferred according to the present invention because of their compatibility with the foam-forming formulations are the acrylate resins such as polymethylacrylate, polyethylacrylate, polyhydroxyethylacrylate and copolymers thereof. These resins are compatible with both the fragrance material to be incorporated into the resin and with the foam-forming formulation.

The thermoplastic and thermosetting resins utilized according to the present invention will have from about 5 to about 70 percent by weight of the fragrance material incorporated therein. Usually at least about 15 percent of the fragrance material is required for effective fragrance emission. Generally it is not possible to incorporate more than about 70 percent by weight of the fragrance material into the resinous material and still obtain the solid characteristic of the resin which is desirable for incorporation of the resin into the foam-forming formulation. The fragrance material can be incorporated into the thermoplastic resin by heating the resin to soften or melt the resin, adding the fragrance material to the softened or melted resin, and thereafter cooling to solidify. The fragrance material can be incorporated into the thermoset resin during the chemical reaction to form the thermosetting material, therefore eliminating some fragrances due to their interference with this chemical reaction. After solidification, the resin can be pelletized or ground, preferably under cryogenic conditions, to obtain a particle size of from about 50 to 450 microns. Above about 450 microns the resin is not easily incorporated into the foam-forming formulation. U.S. Pat. Nos. 3,505,432; 4,051,159; 4,155,897, and 4,356,115 describe fragrance-releasing resins which can be ground and used according to this invention.

The fragrance material which can be utilized according to the present invention is not critical to the extent it is not readily volatile. The fragrances are usually complex mixtures of esters, terpenes, aldehydes, and/or ketones. Virtually any of the conventional fragrance materials can be utilized provided they do not contain functional groups which are reactive with components of the thermosetting or thermoplastic resins and/or the foam-forming components. If they are reactive, the fragrance characteristics will be lost. Exemplary fragrance materials include synthetically formed materials or naturally derived oils such as the oil of bergamot, bitter orange, caraway, cedar leaf, cedar wood, champacc, geranium, lavender, orange, origanum, patchouly, pettitgrin, white cedar, and the like. The particular essential oil or combination of oils to be used depends upon the particular fragrance desired for emission by the product formed.

The polyurethane foam formulations suitable for use according to the present invention are the formulations suitable for making a flexible foam and contain hydroxyl terminated polyether or polyester polyols reactive with organic polyisocyanates in the presence of suitable catalysts, surfactants, and blowing agents. The polyisocyanates which are to be employed in accordance with the present invention are those commonly employed in preparing polyurethane foams and include compounds having the general formula R-$(NCX)_z$, where X may be oxygen or sulfur, z an integer of one or more, and R an organic radical. These isocyanates, therefore, may be either aromatic or aliphatic, or mixed aromatic-aliphatic products. Although it is necessary to have more than 50 percent of z in these reactions equal to at least two to promote polymerization, monofunctional compounds are often desirable to modify the product. Preferred isocyanates are toluene 2,4-diisocyanate, toluene 2,6-diisocyanate,methylene bis (4-phenylisocyanate), 3,3'bitoluene 4,4'diisocyanate, hexamethylenediisocyanate, and octyldecylisocyanate. This preference is based on the commercial availability of such compounds. However, ethylene diisocyanate, trimethylene diisocyanate, tetramethylene diisocyanate, decamethylene diisocyanate, heptylidene diisocyanate, and the corresponding diisothiocyanates; cycloalkylene diisocyanates and diisothiocyanates, e.g., cyclopentylene diisocyanate, cyclohexylene diisocyanate; aromatic diisocyanates and diisothiocyanates, e.g., m-phenylene diisocyanate, napthalene diisocyanate, and diphenyl-4,4'-diisocyanate; aliphatic-aromatic diisocyanates and diisothiocyanates, e.g., xylenel,4-diisocyanate and 4,4'-diphenylenemethane diisocyanate; heterocyclic diisocyanates and diisothiocyanates, such as $SCNCH_2OCH_2NCS$ and $SCN(CH_2)_3$-S-$(CH_2)_3NCS$; the isocyanates and isothiocyanates containing more than two functional groups, e.g., benzene 1,2,4-triisothiocyanate, 1,2,2-triisocyanatobutane, toluene triisocyanate; and as modifiers, the monoisocyanates and monothioisocyanates, e.g., octylisocyanate and octadecylisocyanate, can be selected.

The polyester and polyether polyols for use herein are the conventionally employed polyols for forming flexible polyurethane foams, i.e., polyester and polyether polyols which are reactive with a polyisocyanate under the conditions of the foam-forming reaction in the presence of the various conventional foaming catalysts, surfactants, antioxidants, and the like. The range of molecular weights and range of hydroxyl numbers on the reactive polyols must be consistent with the production of flexible foams. The molecular weight is conventionally from about 1500 up to about 5000 for the polyester polyols, and from about 2000 to about 7000 for the polyether polyols. The hydroxyl number range is from about 20 to about 130, and preferably from about 25 to about 100. It is possible in order to impart special characteristics to the foam, such as through crosslinking, to use in minor amount a polyol having an hydroxyl number of up to 500 and higher.

As is known in the art, a flexible polyurethane foam can be produced by adjusting the polyol and diisocyanate to each other and/or in the presence of low molecular weight crosslinking or curing agents. Additionally, the flexibility characteristics of a polyurethane foam can be modified by using the isocyanate in less than its stoichiometric amount. These flexible foams can have varying degrees of firmness determined by the density characteristics of the foams. It is also possible to include blowing agents such as the Freons or the like to enhance the foaming operation. Since the various materials used are well known to those skilled in the art of polyurethane foams, they will not be described in detail.

It has been found that flame-retardant agents can be incorporated into the foam during the manufacture of the foam without adversely influencing the fragrance-emitting properties of the foam. Flame-retarding agents that can be used are those known in the art for polyurethane foams and include organic and inorganic compounds which contain varying percentages of chlorine and/or bromine, phosphorous, combinations of halogen and phosphorous, and substances such as antimony oxide, hydrated alumina, and compounds containing boron.

To more fully illustrate the present invention, five preferred embodiments of the invention will be set forth. These embodiments will establish that the perfumed resin does not detract from the foam characteristics of a good polyurethane foam while imparting good fragrance-emitting characteristics to the foam. It is to be understood, however, that the examples are illustrative only and are not set forth as being limiting. Parts are by weight throughout unless otherwise designated.

EXAMPLE 1

A foam-forming formulation was made by uniformly mixing in a mixing head 100 parts polyester resin F-76 marketed by Witco Chemical Corporation, Chicago, Ill., which is a glycol adipate ester having a hydroxyl number of approximately 60 and a molecular weight of from about 2000 to 2500; 53.0 parts toluene diisocyanate; 1.50 parts N-ethylmorpholine (NEM); 1.55 parts dimethylcetylamine; 0.30 parts Fomrez 1058 marketed by Witco which is a cell opener based on diethyl ammonium oleate; 1.50 parts M6682A, an organic sulfonated ester surfactant marketed by Witco; 12.0 parts of a fragrance material made up of polyester resin carrier having a viscosity of 500 centiposes and a hydroxyl number of 224 and baby powder resin fragrance in a ratio of 3.5 polyester resin to 1 part resin fragrance, the resin fragrance being a thermosetting polymethylmethacrylate resin carrying 40 percent by weight baby powder fragrance, with water being added to bring the total water content to 4.30 parts. The uniformly blended formulation was applied to a foaming surface to provide a foam upon foaming and curing which was die cuttable with approximately 60 cells per linear inch and a density of approximately 1.6 pounds per cubic foot. The foam will emit a baby powder fragrance for a period of over sixty days.

EXAMPLE 2

A foam-forming formulation was made by uniformly mixing in a mixing head 100 parts polyester resin F-53 marketed by Witco Chemical Corporation having an hydroxyl number of approximately 53; 47.0 parts toluene diisocyanate; 1.50 parts N-ethylmorpholine (NEM); 0.70 parts dimethylcetylamine; 0.30 parts Fomrez 1058; 1.50 parts M6682A organic surfactant; 6 parts of a fragrance material made up of polyester resin as defined in Example 1 and strawberry resin fragrance in a ratio of 4 parts polyester resin to 1 part strawberry resin fragrance, the resin fragrance being a thermosetting polymethylmethacrylate resin carrying 60% by weight strawberry fragrance, with water being added to bring the total water content to 4.30 parts. The formulation upon foaming and curing provided a non-die cuttable foam having a uniform density of 1.8 pounds per cubic foot, a coarse cell size, approximately 40 cells per inch. The foam will emit a strawberry fragrance for a period of over sixty days.

EXAMPLE 3

A foam-forming formulation was made by uniformly mixing in a mixing head 100 parts Fomrez 76 polyester resin; 53 parts toluene diisocyanate; 0.40 parts of a mixture of N,N-dimethylpiperazine (30%) and N,N-dimorpholine diethylether (70%) marketed by Texaco; 0.2 parts 2,6-di-tertbutyl-p-cresol antioxidant marketed by Koppers Co., Inc.; 1.0 parts N-cocomorpholine marketed by Lonza; 0.5 parts cetyl-dimethyl tertiary amine marketed by Lonza, 1.10 parts polyalkyleneoxidemethyl siloxane copolymer surfactant marketed by Union Carbide under the tradename L-536 silicone surfactant; 7.0 parts of a fragrance material made up of a polyester resin carrier as defined in Example 1 and a lavender resin fragrance in a ratio of 2.5 parts polyester resin to 1 part resin fragrance, the resin fragrance being a thermosetting polyethylmethacrylate resin carrying 50 percent by weight lavender oil fragrance, with water being added to bring the total water content to 3.9 parts. The uniformly blended formulation was applied to a foaming surface to provide a foam upon foaming which was die cuttable with a density of approximately 1.6 pounds per cubic foot. The foam will emit a lavender fragrance for a period of over sixty days.

EXAMPLE 4

A foam-forming formulation was made by uniformly mixing in a mixing head 100 parts Fomrez 53 polyester resin; 47 parts toluene diisocyanate; 1.40 parts of a mixture of piperazine (30%) and methoxyethylmorpholine (70%) marketed by Texaco; 0.1 parts 2,6-di-tert-butyl-p-cresol antioxidant marketed by Koppers Co., Inc.; 0.35 parts cetyl-di-methyl tertiary amine marketed by Lonza, 1.10 parts polyalkyleneoxidemethyl siloxane copolymer surfactant marketed by Union Carbide under the tradename L-536 silicone surfactant; 0.60 parts Fomrez 1058; 7.0 parts of a fragrance material made up of a polyester resin carrier as defined in Example 1 and a lavender resin fragrance in a ratio of 2.5 parts polyester resin to 1 part resin fragrance, the resin fragrance being a thermosetting polymethylmethacrylate resin carrying 50 percent by weight lavender oil fragrance, with water being added to bring the total water content to 4.0 parts. The uniformly blended formulation was applied to a foam surface to provide a foam upon foaming which was non-die cuttable with a density of approximately 1.8 pounds per cubic foot. The foam will emit a lavender fragrance for a period of over sixty days.

EXAMPLE 5

A polyether foam-forming formulation was made by uniformly mixing in a mixing head 94 parts of P-774 polyether polyol, a polyoxypropylene-polyoxyethylene polyether polyol having a molecular weight of approximately 3500, a hydroxyl number of 57.6, and a viscosity of 450 centiposes marketed by BASF Wyandotte; 49 parts toluene diisocyanate; 0.4 parts amine catalyst which is a 33 percent solution of triethyldiamine in dipropylene glycol marketed by Dabco; 0.5 parts stannous octoate in dioctylphthalate marketed by Witco under the tradename WC-6; 8.0 parts of a fragrance material made up of P-774 polyether polyol carrier, and a strawberry resin fragrance in a ratio of 3.0 parts polyether resin to 1 part resin fragrance. The resin fragrance being a thermosetting polymethylmethacrylate resin carrying 60 percent by weight strawberry fragrance, with water being added to bring the total water content to 3.7 parts water. The uniformly blended formulation was applied to a foaming surface to provide a polyether foam upon foaming. The foam will emit a strawberry fragrance for a period of over sixty days.

In Examples 1-5 the resin fragrance was prepared by heating the thermosetting resin to soften the resin, with the fragrance being added to the softened resin. After the fragrance was taken up by the softened resin, the resin was cooled to solidify. Upon solidifying, the resin was ground under cryogenic conditions to a particle size of 18 microns.

In Examples 1-5 the resin fragrance can be replaced by other resin fragrances including resin fragrances utilizing thermoplastic resins and fragrance materials to provide any of the desired odors. Additionally, the foam formulation can be modified so as to provide polyether and polyester foams having desired characteristics as known in the art, including flame-retardant foams.

As will be apparent to one skilled in the art, various modifications can be made within the scope of the aforesaid description. Such modifications being within the ability of one skilled in the art form a part of the present invention and are embraced by the appended claims.

It is claimed:

1. A flexible polyurethane foam comprising the foam-forming reaction product of water as a foaming agent, an isocyanate reactive polyol and a polyisocyanate, and including uniformly contained in said foam a fragrance material comprising a finely divided resin carrying a fragrance, said water being present in an amount sufficient to provide a flexible foam and said fragrance material being present in an amount sufficient to provide fragrance-emitting characteristics to said foam for a prolonged time period.

2. The flexible polyurethane foam of claim 1 wherein said resin of said fragrance material is a thermoplastic resin.

3. The flexible polyurethane foam of claim 1 wherein said resin of said fragrance material is a thermosetting resin.

4. The flexible polyurethane foam of claim 2 wherein said thermoplastic resin is a polyacrylic resin.

5. The flexible polyurethane foam of claim 3 wherein said thermosetting resin is a polyacrylate copolymer.

6. The flexible polyurethane foam of claim 1 wherein said reactive polyol is a polyester.

7. The flexible polyurethane foam of claim 1 wherein said reactive polyol is a polyether.

8. The flexible polyurethane foam of claim 1 wherein said finely divided resin has a particle size of about 50 to about 450 microns.

9. The flexible polyurethane foam of claim 8 wherein the finely divided resin has a particle size of about 200 microns.

10. The method of forming a fragrance-emitting flexible polyurethane foam comprising admixing a foam-forming formulation including water as a foaming agent, a reactive polyol, a polyisocyanate, and a fragrance material comprising a finely divided resin carrying a fragrance; subjecting said foaming formulation to foaming conditions to form a flexible polyurethane foam having said fragrance material uniformly contained in said foam, said water being present in an amount sufficient to form a flexible foam and said fragrance material being present in an amount sufficient to provide fragrance-emitting characteristics to said foam for a prolonged time period.

11. The method of claim 10 wherein said resin of said fragrance material is a thermoplastic resin.

12. The method of claim 10 wherein said resin of said fragrance material is a thermosetting resin.

13. The method of claim 11 wherein said thermosetting resin is a polyacrylate copolymer.

14. The method of claim 12 wherein said thermoplastic resin is a polyacrylic resin.

15. The method of claim 10 wherein said reactive polyol is a polyester.

16. The method of claim 10 wherein said reactive polyol is a polyether.

17. The method of claim 10 wherein said finely divided resin has a particle size of about 50 to about 450 microns.

18. The method of claim 17 wherein the finely divided resin has a particle size of about 200 microns.

* * * * *